United States Patent [19]
Jacobs et al.

[11] Patent Number: 5,919,802
[45] Date of Patent: Jul. 6, 1999

[54] METHODS OF PREVENTING AND/OR TREATING TEMPORAL LOBE EPILEPSY

[75] Inventors: Barry L. Jacobs; Elizabeth Gould, both of Princeton, N.J.

[73] Assignee: Princeton University, Princeton, N.J.

[21] Appl. No.: 08/985,766

[22] Filed: Dec. 5, 1997

[51] Int. Cl.⁶ .................. A61K 31/445; A61K 31/495; A61K 31/60; A61K 31/40
[52] U.S. Cl. .................. 514/326; 514/252; 514/253; 514/255; 514/317; 514/318; 514/321; 514/331; 514/411
[58] Field of Search .................. 514/326, 252, 514/253, 255, 317, 318, 321, 331, 411

[56] References Cited

U.S. PATENT DOCUMENTS

| 5,387,593 | 2/1995 | Mattson et al. | 514/326 |
| 5,610,154 | 3/1997 | Cliffe et al. | 514/216 |
| 5,663,191 | 9/1997 | Lavielle et al. | 514/411 |

FOREIGN PATENT DOCUMENTS

| WO 93/13766 | 7/1993 | WIPO . |
| WO 96/04287 | 2/1996 | WIPO . |

OTHER PUBLICATIONS

Azmitia et al. (1996) Neuropsychopharm. 14:35–46.
Bayer et al. (1982) Science 216:890–892.
Blatt et al. (1994) Brain Res. Bull. 34:507–518.
Cameron et al. (1993) Neuroscience 56:337–344.
Cattaneo et al. (1994) Eur. J. Pharmacol. 268:425–430.
Cavalheiro, E.S. (1994) Epilepsia. 35:1–11. (1993).
Cliffe et al. 5–HT1 a receptor antagonists, p. 107.
Debassio (1996) Brain Res. Bull. 41:379–383.
Fanburg et al. (1997) Am. J. Physiol. 272:795–806.
Fornal et al. (1996) J. Pharm. Exp. Therap. 278:752 (Abst. on first page).
Gould et al. (1997) Soc. Neuroscience. (Abstr.) 23:316.
Hayakawa et al. (1994) Neuropsychobiol. 30:53–56.
Kuroda et al. (1994) Brian Res. 648:157–161.
Leite, J.P. (1990) Neuroscience Biobehav. Rev. 14:511–517.
Matsuyama et al. (1996) Brain Res. 728: 175–180.
McKittrick et al. (1995) Bio. Psych. 37:383–393.
Meijer et al. (1994) Eur. J. Pharmacol. 266:255–261.
Parent et al. (1997) J. Neuroscience 17:3727–3738.
Parrott et al. (1991) Atherosclerosis 88:213–218.
Schlessinger et al. (1975) J. Comp. Neurol. 159–149–176.
Stanfield et al. (1988) Exp. Brain. Res. 72:399–406.
Sutula T. (1989) Ann. Neurol. 26:321–330.
Takuwa et al. (1989) Am. J. Physiol. 257:F431–F439.
Tao et al. (1996) J. Neurochem. 66:1067–1075.
Watanabe et al. (1993) Brain Res. 615:87–94.

*Primary Examiner*—Theodore J. Criares
*Attorney, Agent, or Firm*—Klauber & Jackson

[57] ABSTRACT

A method of preventing and/or treating epileptic seizures in a mammal in need of such treatment, which comprises administration to said mammal of a therapeutic amount of a 5HT1A antagonist.

10 Claims, 1 Drawing Sheet

METHODS OF PREVENTING AND/OR TREATING TEMPORAL LOBE EPILEPSY

TECHNICAL FIELD OF THE INVENTION

The present invention relates generally to methods of preventing and/ or treating epilepsy, especially temporal lobe epilepsy, using antagonists of the 5HT1A receptor.

BACKGROUND OF THE INVENTION

Epilepsy, especially temporal lobe epilepsy, is a serious disease which can be of idiopathic or symptomatic origin. Typical treatments include the use of anticonvulsants, such as phenytoin or phenobarbital, to control the characteristic seizures.

The dentate gyrus is a brain region that is critically involved in temporal lobe epilepsy (20). A hallmark of temporal lobe epilepsy is the abnormal organization of mossy fibers, the axons of granule neurons in the dentate gyrus (20). This reorganization of the mossy fiber system is believed to be a major contributor to seizure recurrence in these patients (20). In rats, pilocarpine-induced seizures result in a characteristic sequence of events that ultimately leads to the spontaneous recurrence of seizures several weeks after the initial episode of status epilepticus (12). This experimental method of seizure induction provides an excellent model of temporal lobe epilepsy in humans (12). Recently, it has been speculated that the abnormal mossy fibers produced following pilocarpine-induced seizures originate from granule neurons newly produced in response to the seizures (16). Seizures stimulate the proliferation of granule cell precursors which, in turn, produce abnormal mossy fibers (16). This abnormal mossy fiber production is believed to produce spontaneous recurrent seizures in these animals and thus mimic epilepsy in humans.

In the majority of regions in the mammalian brain, the genesis of neurons is restricted to a discrete time period beginning during gestation and completed within several days. Once this developmental phase ends, neurons differentiate and new neurons cannot be produced. In contrast, the granule cells of the dentate gyrus (part of the hippocampal formation) are formed during an extended period that begins during gestation and continues into adulthood (2, 8).

In adulthood, granule neurons are produced from precursor cells that reside primarily in the subgranular zone, the region between the granule cell layer and hilus (2). It has been demonstrated that these precursor cells proliferate and give rise to immature granule neurons that become incorporated into the granule cell layer and express markers of mature granule neurons, including neuron specific enolase, the calcium binding protein calbindin, and the NMDA receptor subunit NR1, within three weeks of DNA synthesis (4). In addition, these granule neurons produced in adulthood receive synaptic input and extend axons into the mossy fiber pathway (19). The continued production of neurons in the dentate gyrus into adulthood is a common characteristic of most, if not all, mammalian, species, from rodents to primates (2,9).

There have been suggestions that the neurotransmitter serotonin or 5-hydroxytryptamine (5HT) might stimulate the production of granule neurons in the dentate gyrus in adulthood. First, serotonin has been shown to stimulate cell proliferation in many nonneuronal systems (2,5,21). Second, the dentate gyrus is enriched with a specific serotonin receptor subtype (5HT1A) (1) and receives serotonergic innervation from the median raphe nucleus of the brainstem (1). Third, conditions that inhibit granule cell genesis, such as malnutrition (7), high corticosterone (9), stress (9) and NMDA receptor activation, also decrease the density of 5HT fibers or 5HT1A receptors, or inhibit the release of 5HT in the dentate gyrus (3, 14, 15, 22 23). Conversely, experimental manipulations that stimulate granule cell genesis, such as adrenalectomy and NMDA receptor antagonist treatment, also increase the density of 5HT1A receptors or the release of 5HT in the dentate gyrus. (11, 22).

Contrary to the instant invention, compounds which are agonists of the 5HT1A receptor have been suggested as therapeutic agents for the treatment of disease states which exhibit unwanted and abnormal involuntary movements such as those found in epilepsy, parkinsonism, Huntingtons's chorea, tardive dyskinesia, Freidreich's atoxia, presenile dementia, and Gilles de la Tourette's syndrome, see for instance, PCT Published Application WO 93/13766 and PCT Published Application WO 96/04287. These agonists are postulated to inhibit neuronal activity and thus decrease seizure discharge.

In spite of the available therapeutic agents, there remains a need for useful methods of preventing and treating epilepsy in mammalian patients.

SUMMARY OF THE INVENTION

In accordance with the present invention, there is provided a method of preventing and/or treating epileptic seizures in a mammal in need of such treatment, which comprises administration to said mammal of a therapeutic amount of an antagonist to the 5HT1A receptor.

In a still further aspect, the present invention extends to the use of particular 5HT1A antagonists for the prevention and treatment of temporal lobe epilepsy.

The present invention also includes an assay system for screening of potential drugs effective in the treatment of temporal lobe epilepsy in mammals in need of such therapy. In one instance, the test drug could be administered in an assay to determine the antagonist activity to a 5HT1A receptor, to determine its effect thereon, and thereby screen for potential usage as an anti-epileptic agent. This type of assay conveniently can be conducted using cell lines, and thus avoids the more costly and less efficient animal models for the treatment of epilepsy.

Accordingly, it is a principal object of the present invention to provide a method of preventing and/or treating epilepsy, particularly temporal lobe epilepsy, by administration of a pharmaceutically acceptable amount of an antagonist to the 5HT1A receptor.

It is a further object of the present invention to provide a method of screening for agents useful in the treatment of epilepsy, particularly temporal lobe epilepsy, by determining the ability of the potential therapeutic agent to act as an antagonist to the 5HT1A receptor.

It is a still further object of the present invention to prevent and/or treat epilepsy by utilizing a 5HT1A antagonist to prevent and/or reduce the production of abnormal mossy fibers in the temporal lobe of the mammalian brain.

Other objects and advantages will become apparent to those skilled in the art from a review of the ensuing description which proceeds with reference to the following illustrative drawings.

DETAILED DESCRIPTION OF THE INVENTION

Figure 1:
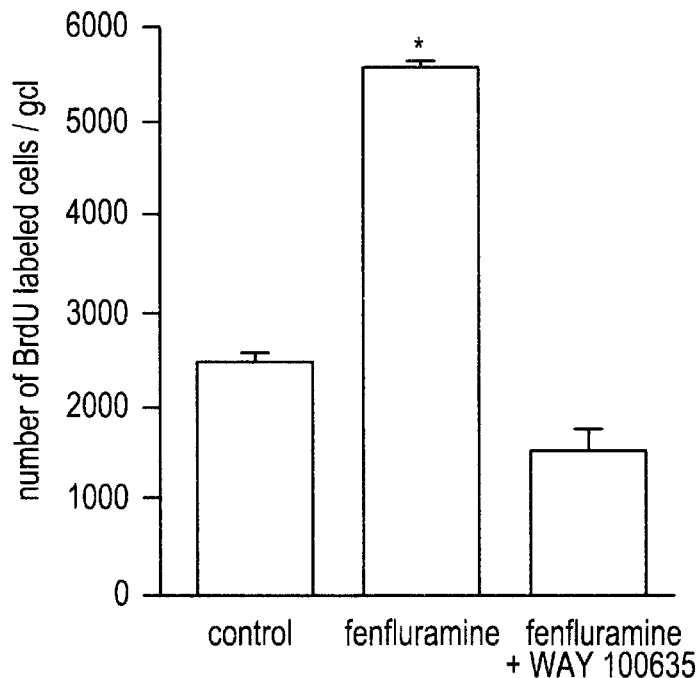
FIG. 1 is a bar graph showing an increase in the number of proliferating cells (bromodeoxyuridine (BrdU) labeled cells) in the dentate gyrus following treatment with fenfluramine (5.0 mg./kg i.p.). Blockade of 5HT1A receptors with N-{2-[4-(methoxyphenyl)-1-piperazinyl]ethyl}-N-(2-pyridinyl) cyclohexanecarboxamide (5.0 mg/kg s.c.) prevented this effect. These rats received an injection of N-{2-[4-(methoxyphenyl)-1-piperazinyl]ethyl}-N-(2-pyridinyl) cyclohexanecarboxamide or saline 30 minutes before and 60 after an injection of fenfluramine or saline. Thirty minutes after fenfluramine injection, the rats were injected with BrdU and perfused after a two (2) hour survival time. Bars represent mean+SEM each obtained from five (5) animals. Asterisk represents significant difference from control ($p<0.005$; ne way ANOVA followed by Tukey HSD post hoc comparisons).

In accordance with the present invention there may be employed conventional pharmaceutical and biological techniques within the skill of the art. Such techniques are explained fully in the scientific and patent literature.

The phrase "pharmaceutically acceptable" refers to molecular entities and compositions that are physiologically tolerable and do not typically produce an allergic or similar untoward reaction, such as gastric upset, dizziness and the like, when administered to a mammal, especially a human.

The phrase "therapeutically effective amount" is used herein to mean an amount sufficient to prevent, or reduce, by at least about 30 percent, more preferably by at least 50 percent, most preferably by at least 90 percent, the occurrence of seizure activity in a patient.

In its primary aspect, the present invention concerns the administration of a therapeutically effective amount of one or more antagonists to the 5HT1A receptor for the prevention and/or treatment of epilepsy, especially temporal lobe epilepsy, in a mammalian patient.

In a particular embodiment, the present invention relates the use of 5HT1A antagonists, particularly those described by Cliffe et al., *The Evolution of Selective, Silent 5HT1A Receptor Antagonists, Current Drugs-Serotonin*, 1993, 99–124, such as the N-{2-[4-(-methoxyphenyl)-1-piperazinyl]ethyl}-N-(2-pyridinyl) cyclohexanecarboxamide, as well as the bicyclic carboxamides disclosed in U.S. Pat. No. 5,610,154, and the piperazinyl- and piperidinyl-cyclohexanols disclosed in U.S. Pat. No. 5,387,593, the disclosures of which are hereby incorporated by reference.

Examples of specific 5HT1A antagonists useful in the present invention are:

N-{2-[4-(2-methoxyphenyl)-1-piperazinyl]ethyl}-N-(2-pyridinyl) cyclohexanecarboxamide;

1-(2-methoxyphenyl)-4-[4-(2-pthalimido)-butyl] piperazine;

4-iodo-N-[2[4-(methoxyphenyl)-1-piperazinyl]ethyl]-N-2-pyridinyl-benzamide hydrochloride;

1-(8-aza-bicyclo[3.2.1]oct-8-yl-4[4-(2-methoxyphenyl)-piperazin-1-yl]-2-phenylbutan-1-one;

1-(8-aza-bicyclo[3.2.1]oct-8-yl-4[4-(5-fluoro-2-methoxyphenyl)-piperazin-1-yl]-2-phenylbutan-1-one;

(+)-(2S)-1-(8-aza-bicyclo[3.2.1]oct-8-yl-4[4-(5-fluoro-2-methoxyphenyl)-piperazin-1-yl]-2-phenylbutan-1-one;

(−)-(2R)-1-(8-aza-bicyclo[3.2.1]oct-8-yl-4[4-(5-fluoro-2-methoxyphenyl)-piperazin-1-yl]-2-phenylbutan-1-one;

1-(8-aza-bicyclo[3.2.1]oct-8-yl-4[4-(1H-indol-4-yl))-piperazin-1-yl-]-2-phenyl-butan-1-one;

(−)-(2R)-1-(8-aza-bicyclo[3.2.1]oct-8-yl-4[4-(1H indol-4-yl)-piperazin-1-yl]-2-phenylbutan-1-one;

1-(8-aza-bicyclo[3.2.1]oct-8-yl-4{4-(2-methoxy-5-trifluoromethyl-phenyl)-piperazin-1-yl]-2-phenylbutan-1-one;

1-(8-aza-bicyclo[3.2.1]oct-8-y)-2-phenyl-4-(pyridin-2-yl-piperzin-1-yl]-butan-1-one;

1-(8-aza-bicyclo[3.2.1]oct-8-yl-4[4-(3-methoxypyridin-2-yl)-piperazin-1-yl]-2-phenylbutan-1-one;

1-(8-aza-bicyclo[3.2.1]oct-8-yl)-2-phenyl-4[4-(3-trifluoromethylpyridin-2-yl-piperazin-1-yl]-butan-1-one;

(8-aza-bicyclo[3.2.1]oct-8-yl)2-phenyl-4-[4-5-trifluoromethyl-pyridin-2-yl)piperazin-1-yl]-butan-1-one;

4-[4-(2-methoxyphenyl)-piperazin-1-yl]-2-phenyl-1(1,3,3-trimethyl-6-azabicyclo[3.2.1]oct-6-yl-butan-1-one;

1-(3-aza-bicyclo[3.2.2]non-3-yl)-4[4-(5-fluoro-2-methoxyphenyl)-piperazin-1-yl]-2-phenylbutan-1-one;

1-(3-aza-bicyclo[3.2.2]non-3-yl)-4[4-(1H-indol-4-yl)-piperazin-1-yl]-2-phenylbutan-1-one;

1-(3-azabicyclo[3.2.1]non-3-yl-4[4-(2-methoxyphenyl)-piperazin-1-yl]-2-phenyl]butan-1-one;

1-(1,3,3a,4,7,7a-hexahydroisoinol-2-yl)-4-chloro-2-phenylbutan-1-one;

1-(1,3,3a,4,7,7a-hexahydroisoinol-2-yl)-4-[-(2-methyoxyphenyl)-2-phenylbutan-1-one;

1-(Octahydroisoindol-2-yl)-4-bromo-2-phenylbutan-1-one;

4-[4-(2-methoxyphenyl)piperazin-1-yl]-1 (octahydroisoindol-2-yl)-2-phenylbutan-1-one;

(+)-(2S)-1-(8-aza-bicyclo[3.2.1]oct-8-y)-4-[4-(1H-indol-4-yl)-piperazin-1-yl]-2-phenyl butan-1-one;

Z-(1,3-benzodioxo[5-yl)-4-[4-(phenylmethyl)-1-piperidinyl]cyclohexanol;

Z-1-(4-methoxyphenyl)-4[4-(phenylmethyl)-1-piperidinyl]cyclohexanol;

Z-1-(1,3-benzodioxol-5-yl)-4-[4-(phenylmethyl)-1-piperazinyl)cyclohexanol;

Z-1-(4-methoxyphenyl)-4[4-(phenylmethyl)-1-piperazinyl]cyclohexanol;

Z-1-[4-(1,3-benzodioxol-5-yl)-4-methoxycyclohexyl)]4-(phenylmethyl)-piperazine;

Z-1-(1,4-benzodioxan-6-yl)-4-[4(phenylmethyl)-1-piperazinyl]cyclohexanol;

E-1-(1,4-benzodioxan-6-yl)-4-[4-phenylmethyl)-1-piperazinyl]cyclohexanol;

Z-1-(1,3-benzodioxol-5-yl)-4-[4-(3-methoxyphenyl)methyl]-1-piperazinyl]cyclohexanol;

Z-1-(1,3-benzodioxol-5-yl)-4-(4[(3-fluorophenyl)methyl)-1-piperazinyl]cyclohexanol;

Z-1-(1,3-benzodioxol-5-yl)-4-[4-[(2-fluorophenyl)methyl]-1-piperazinyl)cyclohexanol;

Z-1-(1,3-benzodioxol-5-yl)-4-[4-(2-methylphenyl)methyl-1-piperazinyl]cyclohexanol;

Z-1-(1,3-benzodioxol-5-yl)-4-[4-[(2-nitrophenyl)methyl]-1-piperazinyl]cyclohexanol;

Z-1-(1,3-benzodioxol-5-yl)-4-[4-[(2-chlorophenyl)methyl]-1-piperazinyl]cyclohexanol;

Z-1-(1,3-benzodioxol-5-yl)-4-[4-(2-thienylmethyl)-1-piperazinyl]cyclohexanol;

Z-1-(1,3-benzodioxol-5-yl)-4-[4-(2,5-dichlorophenyl)-methyl]-1-piperazinyl]cyclohexanol;

Z-1-((1,3-benzodioxol-5-yl)-4-[4-(2,5-difluorophenyl)-methyl]-1-piperazinyl]cyclohexanol;

Z--1-(1,3-benzodioxol-5-yl)-4-[4-(2,5-difluorophenyl)-methyl]-1-piperazinyl]cyclohexanol;

Z-1-(1,3-benzodioxol-5-yl)-4-[4-(3,5-difluorophenyl)-methyl]-1-piperazinyl]cyclohexanol;

Z-1-(1,3-benzodioxol-5-yl)-4-[4-(2-iodophenyl)-methyl]-1-piperazinyl]cyclohexanol;

Z-1-(1,3-benzodioxol-5-yl)-4-[4-(1,3-benzodioxo-4-yl-methyl]-1-piperazinyl]cyclohexanol;

Z-1-(4-fluorophenyl)-4-[4-[(3-methoxyphenyl)methyl]-1-piperazinyl]cyclohexanol;

Z-1-(4-fluorophenyl)-4-[4-[(2-chlorophenyl)methyl]-1-piperazinyl]cyclohexanol;

Z-1-(4-fluorophenyl)-4-[4-[(2,5-difluorophenyl)methyl]-1-piperazinyl]cyclohexanol;

Z-1-[(4-trifluoromethyl)phenyl]-4-[4-[(2-chlorophenyl)-methyl]-1-piperazinyl]cyclohexanol;

Z-1-[(4-trifluoromethyl)phenyl]-4-[4-[(3-methoxyphenyl)methyl]-1-piperazinyl]cyclohexanol;

Z-1-(1,3-benzodioxol-5-yl)-4-[4-[(2-fluoro-5-methoxyphenyl)methyl]-1-piperazinyl]cyclohexanol;

Z-1-(4-fluorophenyl)-4-[4-[(2-fluoro-5-methoxyphenyl)-methyl]-1-piperazinyl]cyclohexanol;

Z-(1,4-benzodioxan-6-yl)-4-[4-[(3-methoxyphenyl)-methyl]-1-piperidinyl]cyclohexanol;

Z-1(1,3-benzodioxol-5-yl)-4-[4-[(3-methoxyphenyl)methyl]-1-piperidinyl]cyclohexanol;

Z-1-(1,3-benzodioxol-5-yl)-4-[4-[(2,5-difluorophenyl)-methyl)-1-piperidinyl]cyclohexanol;

Z-1-[4-(1,3-benzodioxol-5-yl)-4-methoxy-1-cyclohexyl]-4-[(3-methoxyphenyl)methyl]piperidine;

Z-1-[4-(1,4-benzodioxan-6-yl)-4-methoxy-1-cyclohexyl]-4-(3(methoxypheny)methyl]-piperidine);

Z-1-[4-(1,3-benzodioxol-5-yl)-4-methoxy-1-cyclohexyl]-4-[(2,5-difluorophenyl)methyl]piperdine);

Z-1-(4-fluorophenyl)-4-[4-(phenylmethyl)-1-piperidinyl]cyclohexanol;

Z-1-(4-fluorophenyl)-4-[4-[(3-methoxyphenyl)methyl]-1-piperdinyl]cyclohexanol;

Z-1-(4-fluorophenyl)-4-[4-[(2,5-difluorophenyl)methyl]-1-piperdinyl]cyclohexanol;

Z-1-(1,3-benzodioxol-5-yl)-4-[4-[(2-bromophenyl)methyl[-1-piperazinyl]cyclohexanol;

Z-1-(1,3-benzodioxol-5-yl)-4-[4-(diphenylmethyl)-1-piperazinyl]cyclohexanol;

Z-1-(1,3-benzodioxol-5-yl)-4-[4-(1-phenylethyl)-1-piperazinyl]cyclohexanol;

Z-1-[4-(4-fluorophenyl)-4-methoxy-1-cyclohexyl]-4-[(3-methoxyphenyl)methyl]piperazine;

Z-1-[4-(4-fluorophenyl)-4-methoxy-1-cyclohexyl]4-[(3-methoxyphenyl)methyl]piperazine; and the pharmaceutically acceptable salts thereof.

These compounds, as well as numerous other art-recognized 5HT1A antagonists, can be utilized in the therapeutic methods of the present invention to treat and/or prevent epilepsy in susceptible patients.

As stated above, the present invention also relates to a method of screening for potential therapeutic agents which can be utilized in the therapy of epilepsy by virtue of their activity as antagonists to the 5HT1A receptor.

The possibilities both diagnostic and therapeutic that result from the instant invention are due to the determination that activation of 1HT1A receptors during the initial seizures stimulates cell proliferation in the dentate gyrus, thus giving rise to conditions conducive to epileptic seizures. Experiments confirm that blocking the 5HT1A receptor with a 5HT1A antagonist blocks spontaneously occurring neurogenesis in the dentate gyrus and thus a 5HT1A antagonist can be used to block seizure-induced neurogenesis and hence suppress the development of epilepsy. Further experiments have determined that antagonists of the 5HT1A receptor can be utilized to block, and thus prevent, this abnormal cell proliferation in the dentate gyrus, thus preventing and/or minimizing the occurrence of the seizure activity of epilepsy. Additionally, blocking the 5HT1A receptor with a 5HT1A receptor antagonist suppresses neurogenesis and this treatment prevents mossy fiber reorganization, an underlying facet of the development of epilepsy in this animal model and in clinical temporal lobe epilepsy.

Thus, in instances where it is desired to reduce or inhibit the resultant effects of abnormal cell proliferation in the dentate gyrus, the introduction of a 5HT1A antagonist to the patient can be utilized to obviate or minimize the seizure activity, and its reoccurence.

As discussed earlier, antagonists to the 5HT1A receptor have been prepared, and are well-known in the chemical and pharmaceutical literature. These compounds can be formulated as compositions, with a suitable carrier and at a strength effective for administration by various means to a patient suffering from epilepsy, especially temporal lobe epilepsy. A variety of administrative techniques may be utilized, among them, oral, and parenteral techniques such as subcutaneous, intravenous and intraperitoneal injections, catheterizations and the like. Average quantities of the 5HT1A receptor antagonist may vary, and in particular, should be based upon the recommendations and prescription of a qualified physician or veterinarian. Generally, the epileptic seizure control dose is inversely correlatable with the degree of antagonism exhibited at the 5HT1A receptor.

The present invention further contemplates therapeutic compositions useful in practicing the therapeutic methods of this invention. A subject therapeutic composition includes, in admixture, a pharmaceutically acceptable excipient (carrier) and one or more 5HT1A receptor antagonists, as described herein, as active ingredient. In a preferred embodiment, the composition comprises a 1-(2-methoxyphenyl)-4-substituted-1, 4-piperazine with any necessary pharmaceutical adjuvants.

The preparation of therapeutic compositions which contain 5HT1A antagonists is well known in the art. Typically, such compositions are prepared as oral, rectal, transnasal, transdermal or parenteral (i.e., intramuscular, intravenous or subcutaneous) dosage forms, either as tablets, capsules, or liquid solutions or suspensions. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A 5HT1A antagonist can be formulated into the therapeutic composition as its pharmaceutically acceptable salt form. Pharmaceutically acceptable salts include the acid addition salts which are formed with inorganic acids such as, for example, hydrochloric, hydrobromic or phosphoric acids, or such organic acids as acetic, lactic, pyruvic, malonic, maleic, citric, ascorbic, benzoic, cinnamic, oxalic, tartaric, fumaric, mandelic, and the like. Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like. Such salts can exist in either a hydrated or substantially anhydrous form.

Some of the 5HT1A antagonists useful in the present invention contain one or more asymmetric centers and will therefore exist as enantiomers and diastereomers. Contemplated for use in the present invention are the specific optical isomers, racemic mixtures or diasteriomeric mixtures thereof.

The therapeutic 5HT1A antagonist-containing compositions are conventionally administered orally or parenterally, as by ingestion or injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, and the severity of the condition under treatment. Precise amounts of active ingredient required to be administered depend on the judgment of the practitioner and are peculiar to each individual. However, suitable dosages may range from about 0.1 to 20, preferably about 0.5 to about 10, and more preferably 1 to 5, milligrams of active ingredient per kilogram body weight of individual per day, and depend on the route of administration. Typically, the unit dosage form contains from about 0.5 mg to about 750 mg depending upon the activity of the particular 5HT1A antagonist being utilized as the active ingredient.

The present invention also relates to a screening assay for potential therapeutic agents for the treatment of epilepsy. Typically, the test drug is administered in an assay to determine its antagonist activity to the 5HT1A receptor. Quantification of this activity correlates with activity vis a vis the epileptic seizures. Generally, this determination is by a standardized assay, such as that of Alexander et al., *J. Pharm. Pharmacol.*, 1988, 40:888–91. This assay utilizes a rat hippocampal membrane homogenate and test for 5HT1A receptor binding activity.

The following examples are presented in order to more fully illustrate the preferred embodiments of the invention. They should in no way be construed, however, as limiting the broad scope of the invention.

EXAMPLE 1

The effects of the 5HT1A receptor antagonists 1-(2-methoxyphenyl-4[4-(2-phthalimido)piperazine, 4-iodo-N-[2[4-(methoxyphenyl)-1-piperazinyl]ethyl]-N-2-pyridinyl-benzamide hydrochloride or N-{2-[4-(-methoxyphenyl)-1piperazinyl]ethyl}-N-(2-pyridinyl) cyclohexanecarboxamide on spontaneous cell proliferation in the dentate gyrus of intact adult rats were assessed. Adult male rats were treated with 1-(2-methoxyphenyl-4[4-(2-phthalimido)piperazine, (2.5 mg/kg s.c.), 4-iodo-N-[2[4-(methoxyphenyl)-1-piperazinyl]ethyl]-N-2-pyridinyl-benzamide hydrochloride (10 mg/kg s.c.) or N-{2-[4-(-methoxyphenyl)-1-piperazinyl]ethyl}-N-(2-pyridinyl) cyclohexanecarboxamide (5 mg/kg s.c.) and injected with bromodeoxyuridine after 30 minutes. These animals were then perfused after a 2 hour survival time. The results indicate that treatment with any of the above 5HT1A receptor antagonists decreased the number of proliferating cells in the dentate gyrus.

EXAMPLE 2

The treatment of adult rats with the serotonin-releasing drug fenfluramine (5.0 mg/kg i.p.) results in a significant increase in the number of proliferating cells (bromodeoxyuridine (BrdU) labeled cells) in the dentate gyrus (FIG. 1). Treatment with the specific 5-HT1A agonist 8-hydroxy-2-(di-n-propylamino) tetraline also produces this effect, indicating that an action at the 5-HT1A receptor may be crucial. In support of this concept, the aforementioned action of fenfluramine can be prevented by pre-treatment with the specific 5HT1A receptor antagonist N-{2-[4-(-methoxyphenyl)-1-piperazinyl]ethyl}-N-(2-pyridinyl) cyclohexanecarboxamide (5.0 mg/kg s.c.) (FIG. 1) or 1-(2-methoxyphenyl-4[4-(2-phthalimido)piperazine thus further indicating that activation of 5HT1A receptors stimulates cell proliferation in the dentate gyrus.

These rats received an injection of the antagonist or saline 30 minutes before and 60 minutes after an injection of fenfluramine or saline. Thirty (30) minutes after fenfluramine injection, the rats were injected with BrdU and perfused after a 2 hour survival time. Bars in FIG. 1 represent mean+SEM each obtained from 5 animals. The asterisk represents significant difference from control ($p<0.05$; one way ANOVA followed by Tukey HSD post hoc comparisons).

The dentate gyrus is a brain region that is critically involved in temporal lobe epilepsy [Sutula, *Ann Neurol.*, 26:321–330 (1989)]. A hallmark of temporal epilepsy is abnormal organization of mossy fibers, the axons of granule neurons in the dentate gyrus. This reorganization of the mossy fiber system is believed to be a major contribution to seizure recurrence in these patients. In rats, pilocarpine-induced seizures result in a characteristic sequence of events that ultimately leads to the spontaneous recurrence of seizures several weeks after the initial episode of status epilepticus [Leite, *Neurosci Biobehav Rev,* 14:511–517 (1990)]. This experimental method of seizure induction provides an excellent model of temporal lobe epilepsy in humans. A recent study has demonstrated that the abnormal mossy fibers produced following pilocarpine-induced seizures originate from granule neurons newly produced in response to the seizures [Parent et al., *J. Neurosci,* 17:3727–3738 (1997)]. Seizures stimulate the proliferation of granule cells precursors which, in turn, produce abnormal mossy fibers. This abnormal mossy fiber production is believed to produce spontaneous recurrent seizures in these animals. Blocking the production of abnormal mossy fibers, by preventing the seizure-induced stimulation of granule neuron production, prevents the development of temporal lobe epilepsy.

EXAMPLE 3

Figure 2:
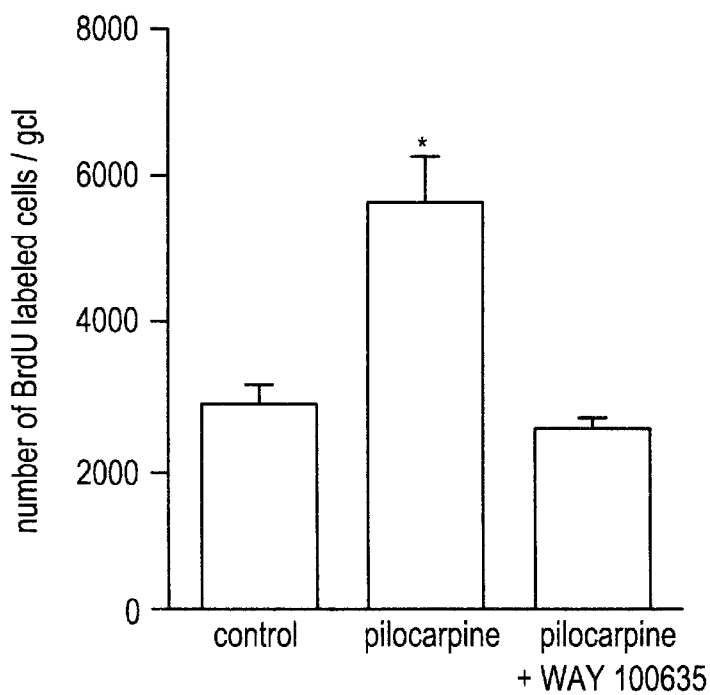
FIG. 2 is a bar graph showing the number of proliferating cells (BrdU labeled cells) in the dentate gyrus increases following pilocarpine-induced status epilepticus. blockade of 5HT1A receptors with N-{2-[4-(-methoxyphenyl)-1-piperazinyl]ethyl}N-(2-pyridinyl) cyclohexanecarboxamide (5 mg/kg s.c.) or saline followed by pilocarpine thirty (30) minutes later. Additional injections of N-{2-[4-(methoxyphenyl)-1-piperazinyl]ethyl}-N-(2-pyridinyl) cyclohexanecarboxamide were performed every 90 minutes thereafter. Two hours after the onset of status epilepticus, the animals were injected with BrdU and perfused one (1) hour later. Bars represent mean+SEM each obtained from five (5) animals. Asterisk represents significant difference from control ($p<0.05$, one way ANOVA followed by Tukey HSD post hoc comparisons).

The results of Example 2 showing that a 5HT1A receptor antagonist prevented the fenfluramine-induced production of new granule neurons (FIG. 1) indicates that seizure-induced stimulation of granule cell genesis may involve serotonin. In fact, previous studies have shown that seizures result in the release of serotonin and increase 5HT1A receptors in the hippocampus [Cavalheiro, *Epilepsia*, 35:1–11 (1994); Hayakawa et al., *Neuropsychobiol* 30:53–56 (1994)]. To test this possibility, status epilepticus was induced in adult rats and the production of granule neurons with, and without, 5HT1A receptor antagonist pretreatment was examined. Pilocarpine-induced seizures resulted in a significant increase in the production of new granule neurons (FIG. 2). This increase can be prevented completely by pretreatment with the 5HT1A receptor antagonist N-{2-[4-(-methoxyphenyl)-1-piperazinyl]ethyl}-N-(2-pyridinyl) cyclohexanecarboxamide (WAY 100635) (5.0 mg/kg s.c.) (FIG. 2) or 1-(2-methyoxyphenyl-4[4-(2-phthalimido)butyl]piperazine.

The number of proliferating cells (BrdU labeled cells) in the dentate gyrus increase following pilocarpine-induced status epilepticus. Blockade of 5HT1A receptors with the 5HT1A antagonist prevented this effect. Rats were injected with THE 5HT1A antagonist N-{2-[4-(-methoxyphenyl)-1-piperazinyl]ethyl}-N-(2-pyridinyl) cyclohexanecarboxamide (5 mg/kg s.c.) or saline followed by pilocarpine thirty (30) minutes later. An additional injection of antagonist was performed sixty (60) minutes after the pilocarpine injection. Two hours after the onset of status epilepticus, the animals were injected with BrdU and perfused 1 hour later. Bars in FIG. 2 represent mean+SEM each obtained from 5 animals. The asterisk represents significant difference from control ($p<0.05$, one way ANOVA followed by Tukey HSD post hoc comparisons).

These studies indicate that activation of 5HT1A receptors stimulates the proliferation of granule cell precursors; and blockade of 5HT1A receptors prevents the production of new granule cells following seizures. Because seizure-induced granule cell genesis and the resulting abnormal mossy fibers contribute to the recurrence of seizures, drugs which block 5HT1A receptors thus have preventative and/or therapeutic effects in temporal lobe epilepsy.

EXAMPLE 4

The effects of chronic treatment with 5HT1A receptor antagonists on the proliferation of granule neurons and the development of abnormal mossy fibers were assessed. Adult male rats were treated with pilocarpine or N-{2-[4-(methoxyphenyl)-1-piperazinyl]ethyl}-N-(2-pyridinyl) cyclohexanecarboxamide followed by pilocarpine. Two hours after the induction of status epilepticus, the seizures were terminated with diazepam and pentobarbital. The rats then received a subcutaneous implant of an osmotic minipump for continuous delivery of either saline or N-{2-[4-(-methoxyphenyl)-1-piperazinyl]ethyl}-N-(2-pyridinyl) cyclohexanecarboxamide in saline. Two weeks later, the animals were injected with bromodeoxyuridine and perfused after a one hour survival time. The brains were processed for BrdU and Timm staining for assessment of the distribution of mossy fibers. The results indicate that 2 weeks of treatment with 5HT1A receptor antagonists persistently suppresses granule cell production and prevents the formation of abnormal mossy fibers in the molecule layer of the dentate gyrus.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

The following is a list of documents related to the above disclosure and particularly to the experimental procedures and discussions. The documents should be considered as incorporated by reference in their entirety.

1. Azmitia, E. C.; Gannon, P. J.; Kheck, N. M.; Whitaker, P. M.-Azmitia, E. C. (1996) Cellular localization of the 5-HT1A receptor in primate brain neurons and glial cells. *Neuropsychopharm.* 14:35–46.

2. Bayer, S. A; Yackel, J. W.; Puri, P. S. (1982) Neurons in the rat dentate gyrus granular layer substantially increase during juvenile and adult life. *Science* 216:890–892.

3. Blatt, G. J.; Chen, J. C.; Rosene, D. L.; Volicer, L.; Galler, J. R. (1994) Prenatal protein malnutrition effects on the serotonergic system in the hippocampal formation: an immunocytochemical, ligand binding and neurochemical study. *Brain Res. Bull.* 34:507–518.

4. Cameron, H. A.; Woolley, C. S.; McEwen, B. S.; Gould, E. (1993) Differentiation of newly born neurons and glia in the dentate gyrus of the adult rat. *Neuroscience* 56:337–344.

5. Cattaneo, M. G.; Palazzi, E.; Bondiolotti, G.; Vincentini, L. M. (1994) 5HT1D receptor type is involved in stimulation of cell proliferation by serotonin in human small cell lung carcinoma. *Eur. J. Pharmacol.* 268:425–430.

6. Cavalheiro, E. S. (1994) Spontaneous recurrent seizures in rats: amino acid and monoamine determination in the hippocampus. *Epilepsia.* 35: 1–11.

7. Debassio, W. A.; Kemper, T. L.; Tonkiss, J.; Galler, J. R. (1996) Effect of prenatal protein deprivation on postnatal granule cell generation in the hippocampal dentate gyrus. *Brain Res. Bull.* 41:379–383.

8. Fanburg, B. L.; Lee, S-L (1997) A new role for an old molecule: serotonin as a mitogen. *Am. J. Physiol.* 272:795–806.

9. Gould, E.; Tanapat, P.; McEwen, B. S.; Flugge, G.; Fuchs, E. (1997) Neurogenesis in the dentate gyrus of adult primates can be suppressed by stress. *Soc. Neuroscience.* (*Abstr.*) 23:316.

10. Hayakawa, H.; Shimizu, M.: Nishida, A.; Motohashi, N.; Yamawaki, S. (1994) Increase in serotonin 1A receptors in the dentate gurus as revealed by autoradiographic analysis following repeated electroconvulsive shock but not imipramine treatment. *Neuropsychobiol.* 30:53–56.

11. Kuroda, Y; Watanabe, Y.; Albeck, D. S.; Hastings, N. B.; McEwen, B. S. (1994) Effects of adrenalectomy and type I or type II glucocorticoid receptor activation on 5-HT1A and 5-HT2 receptor binding and 5-HT transporter mRNA expression in rat brain. *Brain Res.* 648:157–161.

12. Leite, J. P. (1990) Spontaneous recurrent seizures in rats: an experimental model of partial epilepsy. *Neuroscience Biobehav. Rev.* 14:511–517.

13. Matsuyama, S.; Nei, K.; Tanaka, C. (1996) Regulation of glutamate release via NMDA and 5-HT1A receptors in guinea pig dentate gyrus. *Brain Res.* 728:175–180.

14. McKittrick, C. R.; Blanchard, D. C.; Blanchard, R. J.; McEwen, B. S.; Sakai, R. R. (1995) Serotonin receptor binding in a colony model of chronic social stress. *Bio. Psych.* 37:383–393.

15. Meijer, O. C.; deKloet, E. R. (1994) Corticosterone suppresses the expression of 5-HT1A receptor mRNA in the rat dentate gyrus. *Eur. J. Pharmacol.* 266:255–261.

16. Parent, J. M.; Yu, T. W.; Leibowitz, R. T.; Geschwind, D. H.; Sloviter, R. S.; Lowenstein, D. H. (1997) Dentate granule cell neurogenesis is increased by seizures and contributes to aberrant network reorganization in the adult rat hippocampus. *J. Neuroscience* 17:3727–3738.

17. Parrott, D. P.; Lockey, P. M.; Bright, C. P. (1991) Comparison of the mitogenic activity of angiotensin II and serotonin on porcine arterial smooth muscle cells. *Atherosclerosis* 88:213–218.

18. Schlessinger, A. R.; Cowan, W. M.; Gottleib, D. I. (1975) An autoradiographic study of the time of origin and the pattern of granule cell migration in the dentate gyrus of the rat. *J. Comp. Neurol.* 159:149–176.

19. Stanfield, B. B.; Trice, J. E. (1988) Evidence that granule cells generated the dentate gyrus of adult rats extend axonal projections. *Exp. Brain. Res.* 72:399–406.

20. Sutula T. (1989) Mossy Fiber synaptic reorganization in the epileptic human temporal lobe. *Ann. Neurol.* 26:321–330.

21. Takuwa, J.; Ganz, M.; Takuwa, Y.; Sterzel, R. B.; Rasmussen (1989) Studies of the mitogenic effect of serotonin in rat renal mesangial cells. *Am. J. Physiol.* 257:F431–F439.

22. Tao, R.; Auerbach, S. B. (1996) Differential effect of NMDA on extracellular serotonin in rat midbrain raphe and forebrain sites. *J. Neurochem.* 66:1067–1075.

23. Watanabe, Y; Sakai, R. R.; McEwen, B. S.; Mendelson, S. (1993) Stress and antidepressant effects on hippocampal and cortical 5-HT1A and 5-HT2 receptors and transport sites for serotonin. *Brain Res.* 615:87–94.

What is claimed is:

1. A method of preventing and/or treating epileptic seizures in a mammal in need of such treatment, which comprises administration of a therapeutically effective amount of an antagonist to a 5HT1A receptor to said mammal.

2. A method according to claim 1 wherein the 5HT1A antagonist is administered at a dosage of 0.1 to 20 mg/kg body weight per day.

3. A method according to claim 1 wherein the 5HT1A antagonist is administered at a dosage of 1–5 mg/kg body weight per day.

4. A method according to claim 1 wherein the unit dosage of the 5HT1A antagonist is 0.5 mg to 750 mg.

5. A method according to claim 1 wherein the 5HT1A antagonist is a 1-(2-methoxyphenyl)-4-substituted-1,4-piperazine.

6. A method according to claim 1 wherein the 5HT1A antagonist is a bicyclic carboxamide.

7. A method according to claim 1 wherein the 5HT1A antagonist is a piperazinyl-or piperidinyl-cyclohexanol.

8. The method of claim 1 wherein the 5HT1A antagonist is N-{2-[4-(methoxyphenyl)-1-piperazinyl]ethyl}-N-(2-pyridinyl) cyclohexanecarboxamide.

9. The method of claim 1 wherein the 5HT1A antagonist is 1-(2-methyoxyphenyl-4[4-(2-phthalimido)butyl] piperazine.

10. The method of claim 1 wherein the 5HT1A antagonist is 4-iodo-N-[2[4-(methoxyphenyl)-1-piperazinyl]ethyl]-N-2-pyridinyl-benzamide hydrochloride.

* * * * *